(12) United States Patent
Metzger

(10) Patent No.: US 7,695,479 B1
(45) Date of Patent: Apr. 13, 2010

(54) FEMORAL SIZER

(75) Inventor: Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 49 days.

(21) Appl. No.: 11/103,930

(22) Filed: Apr. 12, 2005

(51) Int. Cl.
*A61B 17/60* (2006.01)

(52) U.S. Cl. .................. 606/102; 606/89; 606/86 R

(58) Field of Classification Search ......... 606/86 R–89, 606/102, 96, 104; 623/20.14, 20.21–20.29, 623/20.35, 20.36; 600/587, 592, 594; 33/511, 33/512, 536
See application file for complete search history.

(56) References Cited

U.S. PATENT DOCUMENTS

| | | | |
|---|---|---|---|
| 1,763,730 A | 6/1930 | Von Lackum |
| 1,959,615 A | 5/1934 | Derrah |
| 2,433,815 A | 12/1947 | LaForge |
| 2,455,655 A | 12/1948 | Carroll |
| 2,702,550 A | 2/1955 | Rowe |
| 2,724,326 A | 11/1955 | Long |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie et al. |
| 3,624,747 A | 11/1971 | McKnight et al. |
| 3,631,596 A | 1/1972 | Glaus et al. |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,869,731 A | 3/1975 | Waugh et al. |
| 3,903,549 A | 9/1975 | Deyerle |
| 3,905,105 A | 9/1975 | Tuke et al. |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |

(Continued)

FOREIGN PATENT DOCUMENTS

CH            117960           5/1927

(Continued)

OTHER PUBLICATIONS

"AGC 3000 Intramedullary Surgical Technique Using PMMA Fixation," 1987, Biomet, Inc.

(Continued)

*Primary Examiner*—Eduardo C Robert
*Assistant Examiner*—Tara R George
(74) *Attorney, Agent, or Firm*—Harness, Dickey

(57) ABSTRACT

A femoral sizer. The femoral sizer includes a stylus arm, and a stylus finger coupled to the stylus arm and movable relative to the stylus arm between a first configuration for insertion under soft tissue of a femur and a second configuration for sizing the femur.

2 Claims, 2 Drawing Sheets

U.S. PATENT DOCUMENTS

| | | |
|---|---|---|
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle et al. |
| 4,311,145 A | 1/1982 | Esty et al. |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano et al. |
| 4,501,269 A | 2/1985 | Bagby |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz et al. |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,624,254 A | 11/1986 | McGarry et al. |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,678,470 A | 7/1987 | Nashef et al. |
| 4,682,598 A | 7/1987 | Beraha |
| 4,685,460 A | 8/1987 | Thornton |
| 4,703,751 A | 11/1987 | Pohl |
| 4,711,233 A | 12/1987 | Brown |
| 4,718,413 A | 1/1988 | Johnson |
| 4,718,916 A | 1/1988 | Morscher et al. |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Andergaten et al. |
| 4,935,023 A | 6/1990 | Whiteside et al. |
| 4,936,852 A | 6/1990 | Kent et al. |
| 4,950,296 A | 8/1990 | McIntyre |
| 4,952,213 A * | 8/1990 | Bowman et al. ............... 606/79 |
| 4,961,740 A | 10/1990 | Ray et al. |
| 4,961,954 A | 10/1990 | Goldberg et al. |
| 4,964,865 A | 10/1990 | Burkhead et al. |
| 4,979,949 A | 12/1990 | Matsen, III et al. |
| 4,979,957 A | 12/1990 | Hodorek |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen, III et al. |
| 5,035,700 A | 7/1991 | Kenna |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert et al. |
| 5,092,869 A | 3/1992 | Waldron |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,909 A | 7/1992 | Sutherland |
| 5,147,365 A | 9/1992 | Whitlock et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden et al. |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,702 A | 1/1993 | Bales et al. |
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Michael |
| 5,228,459 A | 7/1993 | Caspari et al. |
| 5,234,433 A | 8/1993 | Bert et al. |
| 5,242,448 A * | 9/1993 | Pettine et al. ............... 606/102 |
| 5,258,004 A | 11/1993 | Bales et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause et al. |
| 5,329,845 A | 7/1994 | Bichel |
| 5,330,468 A * | 7/1994 | Burkhart ............... 606/96 |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,402 A | 11/1994 | Mumme et al. |
| 5,368,599 A | 11/1994 | Hirsch et al. |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| D358,647 S | 5/1995 | Cohen et al. |
| 5,423,827 A | 6/1995 | Mumme et al. |
| 5,425,355 A | 6/1995 | Kulick |
| 5,425,745 A | 6/1995 | Green et al. |

| | | | | | |
|---|---|---|---|---|---|
| 5,443,475 A | 8/1995 | Auerbach et al. | 5,817,097 A | 10/1998 | Howard et al. |
| 5,445,639 A | 8/1995 | Kuslich et al. | 5,817,109 A | 10/1998 | McGarry et al. |
| 5,445,642 A | 8/1995 | McNulty et al. | 5,842,477 A | 12/1998 | Naughton et al. |
| 5,454,365 A | 10/1995 | Bonutti | 5,846,931 A | 12/1998 | Hattersley et al. |
| 5,454,815 A | 10/1995 | Geisser et al. | 5,860,980 A | 1/1999 | Axelson, Jr. et al. |
| 5,454,816 A | 10/1995 | Ashby | 5,860,981 A | 1/1999 | Bertin et al. |
| 5,456,268 A | 10/1995 | Bonutti | 5,866,415 A | 2/1999 | Villeneuve |
| 5,464,407 A * | 11/1995 | McGuire ................. 606/86 | 5,871,493 A | 2/1999 | Sjostrom et al. |
| 5,472,415 A | 12/1995 | King et al. | 5,879,354 A | 3/1999 | Haines et al. |
| 5,484,095 A | 1/1996 | Green et al. | 5,888,219 A | 3/1999 | Bonutti |
| 5,486,178 A * | 1/1996 | Hodge ..................... 606/82 | 5,899,914 A | 5/1999 | Zirps et al. |
| 5,490,854 A | 2/1996 | Fisher et al. | 5,908,424 A | 6/1999 | Bertin et al. |
| 5,497,933 A | 3/1996 | DeFonzo et al. | 5,911,723 A | 6/1999 | Ashby et al. |
| 5,507,763 A | 4/1996 | Petersen et al. | 5,913,874 A | 6/1999 | Berns et al. |
| 5,514,139 A | 5/1996 | Goldstein et al. | 5,916,219 A | 6/1999 | Matsuno et al. |
| 5,514,143 A | 5/1996 | Bonutti et al. | 5,921,990 A | 7/1999 | Webb |
| 5,520,692 A | 5/1996 | Ferrante | 5,925,049 A | 7/1999 | Gustilo et al. |
| 5,520,694 A | 5/1996 | Dance et al. | 5,961,499 A | 10/1999 | Bonutti et al. |
| 5,522,897 A | 6/1996 | King et al. | 5,997,566 A | 12/1999 | Tobin |
| 5,540,695 A | 7/1996 | Levy | 6,007,537 A | 12/1999 | Burkinshaw et al. |
| 5,545,222 A | 8/1996 | Bonutti | 6,012,456 A | 1/2000 | Schuerch |
| 5,546,720 A | 8/1996 | LaBruzza | 6,015,419 A | 1/2000 | Strome et al. |
| 5,549,683 A | 8/1996 | Bonutti | 6,019,767 A | 2/2000 | Howell |
| 5,554,169 A | 9/1996 | Green et al. | 6,022,350 A | 2/2000 | Ganem et al. |
| 5,562,675 A * | 10/1996 | McNulty et al. ......... 606/96 | 6,024,746 A | 2/2000 | Katz |
| 5,569,163 A | 10/1996 | Francis et al. | 6,056,754 A | 5/2000 | Haines et al. |
| 5,569,261 A | 10/1996 | Marik et al. | 6,056,756 A | 5/2000 | Eng et al. |
| 5,570,700 A | 11/1996 | Vogeler | 6,059,817 A | 5/2000 | Bonutti et al. |
| 5,578,039 A | 11/1996 | Vendrely et al. | 6,059,831 A | 5/2000 | Braslow et al. |
| 5,593,448 A | 1/1997 | Dong | 6,063,095 A | 5/2000 | Wang et al. |
| 5,597,379 A | 1/1997 | Haines et al. | 6,077,270 A | 6/2000 | Katz |
| 5,608,052 A | 3/1997 | Zmitek et al. | 6,077,287 A | 6/2000 | Taylor et al. |
| 5,609,603 A | 3/1997 | Linden | 6,086,593 A | 7/2000 | Bonutti |
| 5,624,444 A | 4/1997 | Wixon et al. | 6,090,122 A | 7/2000 | Sjostrom et al. |
| 5,624,463 A | 4/1997 | Stone et al. | 6,096,043 A | 8/2000 | Techiera et al. |
| 5,632,745 A | 5/1997 | Schwartz | 6,099,531 A | 8/2000 | Bonutti |
| 5,643,272 A | 7/1997 | Haines et al. | 6,099,532 A | 8/2000 | Florea |
| 5,649,946 A | 7/1997 | Bramlet | 6,102,850 A | 8/2000 | Wang et al. |
| 5,649,947 A | 7/1997 | Auerbach et al. | 6,106,529 A | 8/2000 | Techiera |
| 5,653,714 A | 8/1997 | Dietz et al. | 6,118,845 A | 9/2000 | Simon et al. |
| 5,659,947 A | 8/1997 | Eilers et al. | 6,120,509 A | 9/2000 | Wheeler |
| 5,662,656 A * | 9/1997 | White ..................... 606/88 | 6,132,472 A | 10/2000 | Bonutti |
| 5,662,710 A | 9/1997 | Bonutti | 6,156,070 A | 12/2000 | Incavo et al. |
| 5,667,069 A | 9/1997 | Williams, Jr. | 6,159,246 A | 12/2000 | Mendes et al. |
| 5,667,511 A | 9/1997 | Vendrely et al. | 6,171,340 B1 | 1/2001 | McDowell |
| 5,667,512 A | 9/1997 | Johnson | 6,174,321 B1 | 1/2001 | Webb |
| 5,667,520 A | 9/1997 | Bonutti | 6,185,315 B1 | 2/2001 | Schmucker et al. |
| D385,163 S | 10/1997 | Hutchins et al. | 6,187,023 B1 | 2/2001 | Bonutti |
| 5,681,316 A | 10/1997 | DeOrio et al. | 6,195,158 B1 | 2/2001 | Cadell et al. |
| 5,683,398 A | 11/1997 | Carls et al. | 6,197,064 B1 | 3/2001 | Haines et al. |
| 5,688,279 A | 11/1997 | McNulty et al. | 6,198,794 B1 | 3/2001 | Peshkin et al. |
| 5,688,280 A | 11/1997 | Booth, Jr. et al. | 6,211,976 B1 | 4/2001 | Popovich et al. |
| 5,694,693 A | 12/1997 | Hutchins et al. | 6,214,051 B1 | 4/2001 | Badorf et al. |
| 5,702,447 A | 12/1997 | Walch et al. | 6,228,121 B1 | 5/2001 | Khalili |
| 5,702,475 A | 12/1997 | Zahedi et al. | 6,258,127 B1 | 7/2001 | Schmotzer et al. |
| 5,704,941 A | 1/1998 | Jacober et al. | 6,277,136 B1 | 8/2001 | Bonutti |
| 5,707,350 A | 1/1998 | Krause et al. | 6,290,703 B1 | 9/2001 | Ganem et al. |
| 5,712,543 A | 1/1998 | Sjostrom | 6,290,704 B1 | 9/2001 | Burkinshaw et al. |
| 5,716,360 A | 2/1998 | Baldwin et al. | 6,325,806 B1 | 12/2001 | Fox |
| 5,718,708 A | 2/1998 | Webb | 6,328,572 B1 | 12/2001 | Higashida et al. |
| 5,720,752 A | 2/1998 | Elliott et al. | 6,338,737 B1 | 1/2002 | Toledano et al. |
| 5,723,331 A | 3/1998 | Tubo et al. | 6,358,266 B1 | 3/2002 | Bonutti |
| 5,733,292 A | 3/1998 | Gustilo et al. | 6,361,565 B1 | 3/2002 | Bonutti |
| 5,749,876 A | 5/1998 | Duvillier et al. | 6,391,040 B1 | 5/2002 | Christoudias |
| 5,755,731 A | 5/1998 | Grinberg | 6,406,495 B1 | 6/2002 | Schoch et al. |
| 5,755,791 A | 5/1998 | Whitson et al. | 6,409,722 B1 | 6/2002 | Hoey et al. |
| 5,755,803 A | 5/1998 | Haines et al. | 6,423,063 B1 | 7/2002 | Bonutti |
| 5,769,855 A | 6/1998 | Bertin et al. | 6,431,743 B1 | 8/2002 | Mizutani et al. |
| 5,769,899 A | 6/1998 | Schwartz et al. | D462,767 S | 9/2002 | Meyer et al. |
| 5,772,594 A | 6/1998 | Barrick | 6,458,135 B1 * | 10/2002 | Harwin et al. ............. 606/88 |
| 5,788,700 A | 8/1998 | Morawa et al. | 6,468,280 B1 | 10/2002 | Saenger et al. |
| 5,810,827 A | 9/1998 | Haines et al. | 6,468,289 B1 | 10/2002 | Bonutti |
| 5,810,831 A | 9/1998 | D'Antonio | 6,478,799 B1 | 11/2002 | Williamson |

| | | | |
|---|---|---|---|
| 6,482,209 B1 | 11/2002 | Engh et al. | |
| 6,500,181 B1 | 12/2002 | Portney | |
| 6,503,267 B2 | 1/2003 | Bonutti et al. | |
| 6,554,837 B1 | 4/2003 | Hauri et al. | |
| 6,554,838 B2 | 4/2003 | McGovern et al. | |
| 6,558,391 B2 | 5/2003 | Axelson, Jr. et al. | |
| 6,575,982 B1 | 6/2003 | Bonutti | |
| 6,602,259 B1 | 8/2003 | Masini | |
| 6,620,181 B1 | 9/2003 | Bonutti | |
| 6,632,225 B2 | 10/2003 | Sanford et al. | |
| 6,635,073 B2 | 10/2003 | Bonutti | |
| 6,673,077 B1 | 1/2004 | Katz | |
| 6,676,662 B1 | 1/2004 | Bagga et al. | |
| 6,695,848 B2 | 2/2004 | Haines | |
| 6,702,821 B2 | 3/2004 | Bonutti | |
| 6,770,078 B2 | 8/2004 | Bonutti | |
| 6,916,325 B2 * | 7/2005 | Kana et al. | 606/89 |
| 6,979,299 B2 | 12/2005 | Peabody et al. | |
| 7,029,477 B2 | 4/2006 | Grimm | |
| 7,172,599 B2 * | 2/2007 | Steffensmeier et al. | 606/102 |
| 7,261,719 B1 | 8/2007 | Twomey et al. | |
| 2001/0018589 A1 | 8/2001 | Muller | |
| 2001/0034554 A1 | 10/2001 | Pappas | |
| 2001/0037155 A1 | 11/2001 | Merchant | |
| 2002/0029038 A1 | 3/2002 | Haines | |
| 2002/0029045 A1 | 3/2002 | Bonutti | |
| 2002/0052606 A1 | 5/2002 | Bonutti | |
| 2002/0116023 A1 | 8/2002 | Fletcher et al. | |
| 2002/0173797 A1 | 11/2002 | Van Zile et al. | |
| 2002/0198529 A1 | 12/2002 | Masini | |
| 2002/0198531 A1 | 12/2002 | Millard et al. | |
| 2003/0028196 A1 | 2/2003 | Bonutti | |
| 2003/0060831 A1 | 3/2003 | Bonutti | |
| 2003/0100906 A1 | 5/2003 | Rosa et al. | |
| 2003/0100907 A1 | 5/2003 | Rosa et al. | |
| 2003/0130665 A1 | 7/2003 | Pinczewski et al. | |
| 2003/0171757 A1 | 9/2003 | Coon et al. | |
| 2003/0212403 A1 | 11/2003 | Swanson | |
| 2003/0216741 A1 | 11/2003 | Sanford et al. | |
| 2003/0220641 A1 | 11/2003 | Thelen et al. | |
| 2003/0225413 A1 | 12/2003 | Sanford et al. | |
| 2004/0039395 A1 | 2/2004 | Coon et al. | |
| 2004/0102785 A1 | 5/2004 | Hodorek et al. | |
| 2004/0138670 A1 | 7/2004 | Metzger | |
| 2004/0220583 A1 * | 11/2004 | Pieczynski et al. | 606/102 |
| 2004/0267271 A9 * | 12/2004 | Scribner et al. | 606/92 |
| 2005/0049603 A1 | 3/2005 | Calton et al. | |
| 2005/0113840 A1 | 5/2005 | Metzger et al. | |
| 2005/0149042 A1 | 7/2005 | Metzger | |
| 2005/0177170 A1 | 8/2005 | Fisher et al. | |
| 2006/0058810 A1 * | 3/2006 | Wozencroft et al. | 606/102 |
| 2006/0095049 A1 * | 5/2006 | Zannis et al. | 606/102 |
| 2006/0142774 A1 | 6/2006 | Metzger | |
| 2006/0142778 A1 * | 6/2006 | Dees | 606/88 |
| 2007/0083209 A1 | 4/2007 | Schenberger et al. | |
| 2007/0233140 A1 | 10/2007 | Metzger et al. | |
| 2007/0282451 A1 | 12/2007 | Metzger et al. | |

FOREIGN PATENT DOCUMENTS

| | | |
|---|---|---|
| DE | 337437 | 5/1921 |
| FR | 1111677 | 3/1956 |
| JP | 2501806 | 6/1990 |
| JP | 3504337 | 9/1991 |
| JP | 7178114 | 7/1995 |
| WO | WO-8804912 | 7/1988 |
| WO | WO-8909028 | 10/1989 |
| WO | WO 96/07361 | 3/1996 |
| WO | WO 9729703 | 8/1997 |

OTHER PUBLICATIONS

"AGC Distal Fem Cutter for Dr. Hardy," Biomet, Inc., Jun. 22, 1989.
"AGC Total Knee System, Intramedullary Without Distractor Surgical Technique," 1989, Biomet, Inc.
"AGC Traditional Surgical Overview", copyright 2001 Biomet Orthopedics, Inc.
"AGC-S Total Knee System, Surgical Technique for the AGC-S Total Knee System," 1992, Biomet, Inc.
"Anatomic Axial Alignment Instrumentation," 1994, Biomet, Inc.
"The AGC Revision Knee System Surgical Technique," 1997 Biomet, Inc.
Genus, brochure entitled "Uni Knee System," Biomet, Inc., Nov. 15, 1998.
Insall/Burstein II Modular Knee System by Zimmer, Inc. copyright 1989.
Keys, Graham W., "Reduced Invasive Approach for Oxford II Medial Unicompartmental Knee Replacement—a Preliminary Study," The Knee, (1999) pp. 193-196.
MIS Minimally Invasive Solution The M/G Unicompartmental Knee Minimally Invasive Surgical Technique, by Zimmer copyright 2000.
Scorpio! Single Axis Total Knee System—Passport Total Knee Instruments—Passport A.R. Surgical Technique by Sryker Howmedica Osteonics, Copyright 2000.
Simple Instruments Surgical Technigue for the Knee, copyright 2000 Biomet, Inc.
The Oxford, brochure entitled "Unicompartmental Knee System", Biomet Orthopedics, Inc., Jul. 15, 2004.
"Hand Instruments", High Performance, Precision Series brochure by Arthrotek, copyright 2000.

* cited by examiner

FEMORAL SIZER

Various femoral sizers are known for sizing the femur in knee procedures. As surgical knee procedures have been evolving that can reduce the length of the procedure, trauma to associated tissues, and time for recovery, new femoral sizers that can be used in either standard or newer procedures are desirable.

SUMMARY

The present teachings provide a femoral sizer that includes a stylus arm, and a stylus finger coupled to the stylus arm and movable relative to the stylus arm between a first configuration for insertion under soft tissue of a femur and a second configuration for sizing the femur.

The present teachings also provide a method for sizing a femur. The method includes moving a stylus finger coupled to a stylus arm of a femoral sizer to a non-engaging configuration, inserting the stylus arm through an incision and under femoral tissue, moving the stylus finger to an engaging configuration, and moving the stylus arm over the femur for sizing the femur.

The present teachings provide a femoral sizer that includes a base configured for positioning adjacent a distal femur, a coupler adjustably connected to the base, a stylus arm slidably connected to the coupler, and a stylus finger coupled to the stylus arm and movable between a non-engaging configuration for insertion under soft tissue of a femur and an engaging configuration for sizing the femur.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses.

Figure 1:
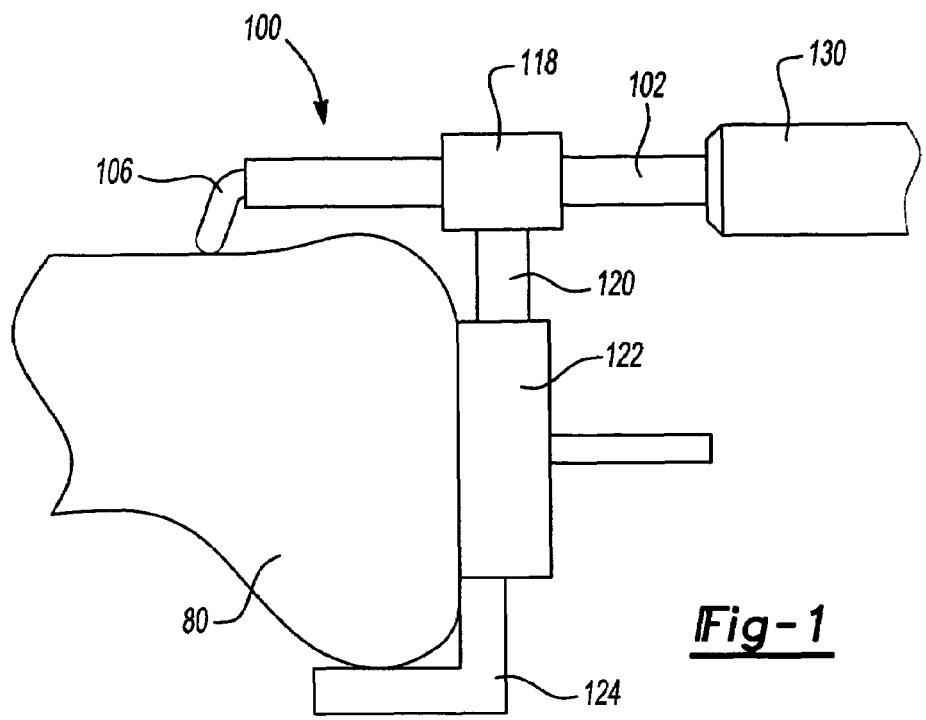
FIG. 1 is an environmental side view of a femoral sizer according to the present teachings, the sizer shown coupled on a femur.

Referring to FIG. 1, an exemplary femoral anterior-posterior sizer 100 according to the present teachings can include a sizer base 122, and a stylus arm 102 having a stylus finger 106 movably coupled thereto. The stylus arm 102 can be adjustably coupled to the base 122, for example, by a coupler 120, allowing the stylus finger 106 to track the anterior surface of the femur 80 for sizing the femur 80 according to known sizing procedures. The coupler 120 can be, for example, an elongated element that is rotatably and slidably received in a bore or other opening of the base 122, although other known coupling devices and methods can also be used, including integral, or bent or modular configurations and connections. The stylus arm 102 can be engaged to the coupler 120 by a connector 118, which can be, for example, a tubular element or bearing slidably receiving the stylus arm 102 permitting both superior-inferior and anterior-posterior movement of the stylus arm 102 and the stylus finger 106. The connector 118 can also be integral with the stylus arm 102. The base 122 can include scale indicia for indicating the anterior-posterior size of the femur 80 as the stylus finger 106 moves over the anterior surface of the femur 80.

The stylus arm 102 can pivot about a center axis of the coupler 120, enabling a corresponding rotational movement for the stylus finger 106. The sizer 100 can also include a pair of feet or other support 124 adapted to be positioned under the posterior condyles of the femur 80. All or some of the parts of the sizer 100 can be modularly interconnected. The stylus arm 102 can be also provided with an ergonomic, quick-connect, pistol-grip, or other known handle 130 for facilitating moving the stylus arm 102 and/or the stylus finger 106, as desired.

Figure 2:
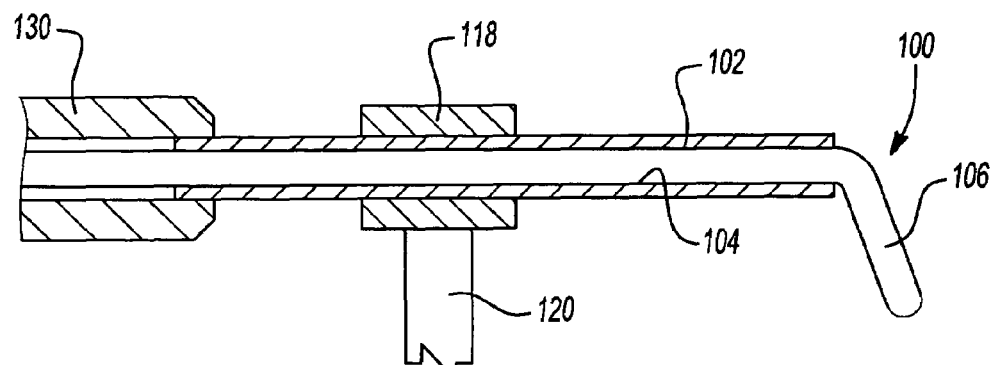
FIG. 2 is a sectional view of a stylus arm and a movable finger of a femoral sizer according to the present teachings, the stylus finger shown in an engaging configuration.
Figure 3:
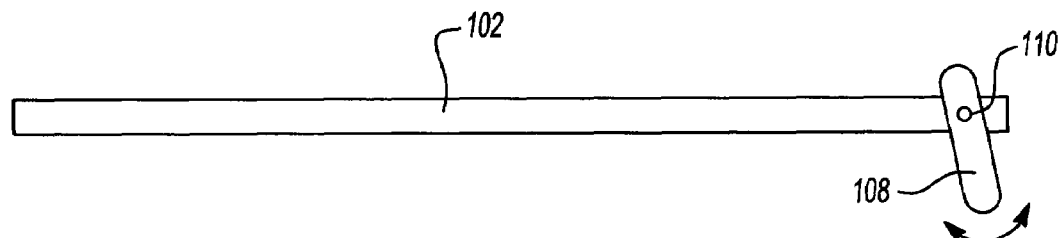
FIG. 3 is a sectional view of a stylus arm having a pivotable finger for a femoral sizer according to the present teachings.

The sizer 100 can have a streamlined profile with reduced dimensions to accommodate the confines of small incisions, should such be desired by the surgeon, as may be practiced in minimally invasive procedures. Further, the stylus finger 106 can be configured for easy insertion under soft tissue during a knee procedure. Referring to FIGS. 2 and 3, the stylus finger 106 can be a structure or portion thereof which is movable or configurable between a compact, non-engaging position/configuration for insertion into the incision and an extended or engaging position/configuration for anterior-posterior sizing of the femur. In the non-engaging position, the stylus finger 106 can be withdrawn, retracted, pivoted onto the stylus arm 102, collapsed, folded, bent or otherwise configured not to protrude significantly outward from the stylus arm 102 or engage the femur 80.

Figure 2A:
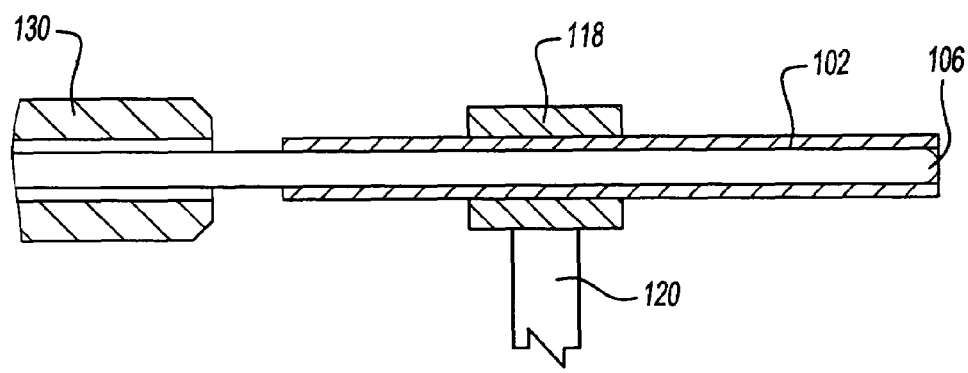
FIG. 2A is a sectional view of the stylus arm of FIG. 2, showing the stylus finger in a non-engaging configuration according to the present teachings.

Referring to FIGS. 2 and 2A, the stylus finger 106 can be a bendable or deformable elongated or wire-like element made of biocompatible material, such as stainless steel, superelastic material, such nitinol, for example, or other material. The stylus finger 106 can be received in a guiding bore 104 of the stylus arm 102 and can movable between an extended or femur-engaging position for sizing the femur 80, as illustrated in FIG. 2, and a retracted, non-engaging position illustrated in FIG. 2A for insertion under femoral tissue. When the stylus finger 106 is made of superelastic material, the superelastic material can be trained to assume a curved shape that is angled relative to the straight stylus arm 102 outside the bore 104. When the stylus finger 106 is made of untrained superelastic material or other bendable material, the stylus finger 106 can be bent to a desirable shape.

Referring to FIG. 3, the stylus finger 106 can be a pivotable element 108 that can pivot about a pivot pin 110, such that the pivotable element 108 can collapse in a direction substantially coaxial to the stylus arm 102 to facilitate insertion under the soft tissue. The pivotable element 108 can be freely pivotable, but it can also be biased in the femur-engaging position shown in FIG. 3, by using a spring, a cam or other known biasing elements, such that the pivotable element 108 returns to the engaging position when no counter-biasing force is applied to hold the pivotable element 108 in the non-engaging position. Further, the pivotable element 108 can be controllable with any known actuator that can be attached to the stylus arm 102 or to the handle 130. For example, the motion of the pivotable element 108 and the associated actuation can be effected by known devices and methods, including cable actuators, or ratchet and spool actuators, movable rod actuators or the actuators and devices disclosed in co-owned U.S. Pat. Nos. 5,443,475 and 5,649,947, the disclosures of which are incorporated herein by reference in their entirety.

Referring to FIG. 1, in an exemplary knee procedure, the sizer 100 can be placed flush with the distal femur 80, which has been exposed through an incision. The stylus finger 106 can be moved to the non-engaging configuration, for example by retracting the stylus finger 106 as illustrated in FIG. 2A or by pivoting the stylus finger 106 as illustrated in FIG. 3. The stylus arm 102 with the stylus finger 106 in the non-engaging configuration can be then inserted under soft tissue exposed by the incision. The non-engaging configuration enables the sizer 100 to be conveniently used in a small incision during minimally invasive procedures. Using the handle 130 or an actuator coupled to the handle 130, the stylus finger 106 can be extended and moved along the anterior femoral surface to determine the size of the femur 80.

It will be appreciated that the reconfigurable stylus finger 106 of the present teachings can be coupled to the stylus arm of any known femoral sizer and is not limited to the exemplary sizer illustrated herein. For example, the stylus finger 106 can be used with any of the femoral sizers disclosed in co-owned U.S. patent application Ser. No. 11/058,527, filed on Feb. 15, 2005, entitled "Instrumentation of Knee Resection", the disclosure of which is incorporated herein by reference.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A femoral sizer for sizing a femur, comprising:
a stylus that moves between a first engaging position relative to the femur and a second non-engaging position, the stylus having an arm portion and a finger portion, the arm portion defining a first longitudinal axis between a first proximal end and a first distal end, the finger portion having an entire length between a second proximal end and a second distal end, the second distal end defining a terminal tip of the stylus, the finger portion being linear along its length and defining a second longitudinal axis wherein the stylus transitions between the arm portion and the finger portion at a transition defined at the first distal end and the second proximal end, wherein the first and second longitudinal axes are parallel in the first non-engaging position and diverge at the transition in the second engaging position wherein the terminal tip is engagable with an anterior surface of the femur during sizing of the femur and wherein the first engaging position and the second non-engaging position are distinct;
wherein the transition is defined by a pivot pin coupled through the first distal end and the second proximal end, wherein the finger portion rotates relative to the arm portion about the pivot pin between the engaging position and a non-engaging position; and
wherein the pivot pin defines a pivot axis, wherein the pivot axis is substantially transverse to the first and second longitudinal axes and is non-intersecting with the femur.

2. A femoral sizer for sizing a femur, comprising:
a stylus having an arm portion and a finger portion, the finger portion defining a distal tip of the stylus that is engageable with an anterior surface of the femur, the finger portion coupled to the arm portion with a pivot pin and pivotable about the pivot pin relative to the arm portion between a first configuration wherein the finger portion is substantially parallel with the arm portion and insertable under soft tissue of the femur, and a second configuration wherein the finger portion is oriented at a non-zero angle relative to the arm portion for engaging the anterior surface of the femur during sizing of the femur, wherein the finger portion is substantially linear along its length and defines a first axis that extends through the distal tip and the pivot pin and wherein the arm portion defines a second axis that extends through a proximal end of the finger portion and the pivot pin, wherein the first and second axes are substantially parallel in the first configuration and substantially non-parallel in the second configuration;
wherein the pivot pin defines a pivot axis that is non-intersecting with the femur.

* * * * *